United States Patent [19]

Mattioli et al.

[11] Patent Number: 5,179,466
[45] Date of Patent: Jan. 12, 1993

[54] DEVICE FOR PROJECTING LIGHT SPOTS ONTO A SURFACE

[75] Inventors: Renzo Mattioli, Rome; Fausto Fiorini, Monteguerrano-Sutri, both of Italy

[73] Assignee: Optikon Oftalmologia S.p.A., Rome, Italy

[21] Appl. No.: 557,611

[22] Filed: Jul. 24, 1990

[30] Foreign Application Priority Data

Jul. 31, 1989 [IT] Italy .............................. 48259 A/89

[51] Int. Cl.⁵ .......................... G02B 26/02; A61B 3/02
[52] U.S. Cl. ...................................... 359/234; 351/224
[58] Field of Search ............... 350/266, 273, 314, 574; 351/226, 223, 224; 359/227, 234, 503, 888

[56] References Cited

U.S. PATENT DOCUMENTS 4,260,227  4/1981  Munnerlyn et al. ................. 351/226
4,561,738 12/1985  Humphrey et al. ................. 351/226

*Primary Examiner*—Bruce Y. Arnold
*Assistant Examiner*—James Phan
*Attorney, Agent, or Firm*—Trexler, Bushnell, Giangiorgi & Blackstone, Ltd.

[57] ABSTRACT

A device for projecting light spots onto a surface, comprising a device for generating and concentrating light, a pierced member which is movable before said device and endowed with means for selecting the hole to be aligned with the light, an assembly of lenses and mirrors and a projection head for projecting light onto a surface, and a shutter member, which controls the projection of the beam itself, in which device means for orienting said pierced member around the vertical axis passing through the center of the selected hole and means for orienting the same pierced member around the horizontal axis passing through the center of the selected hole are provided; the orientation and position of the pierced member, as well as the selection of the hole and of the orientation of the projection head, being achieved by a computer.

21 Claims, 10 Drawing Sheets

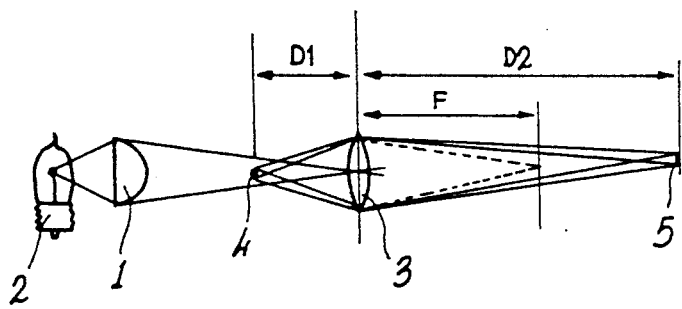
FIG.1
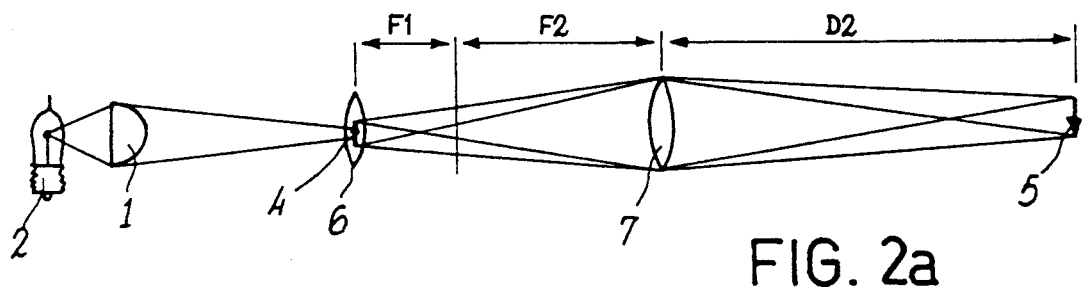
FIG. 2a
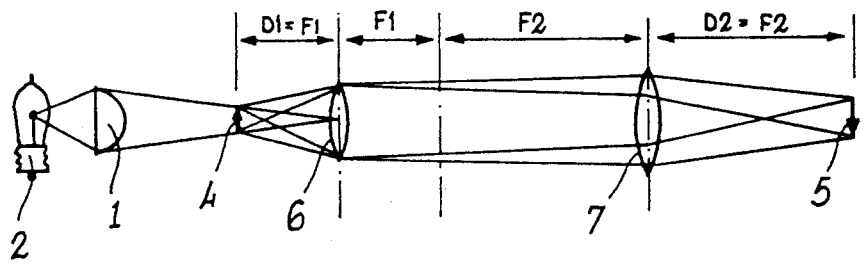
FIG. 2b
FIG. 2c
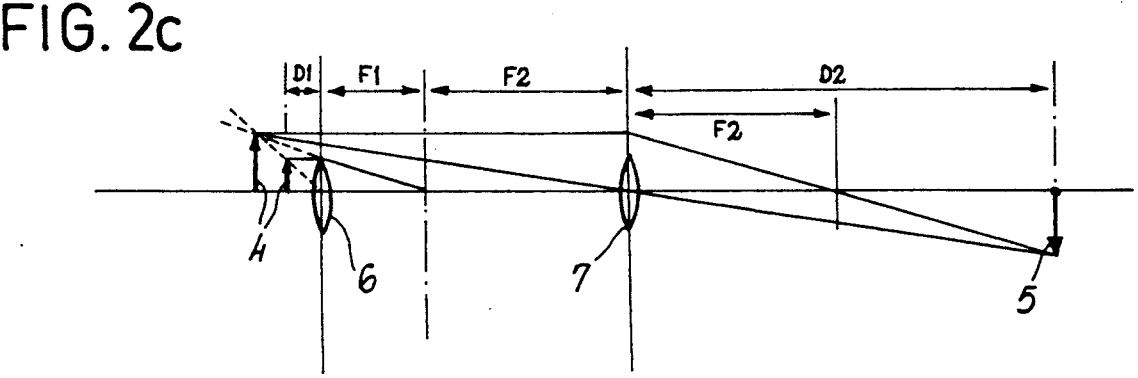

DEVICE FOR PROJECTING LIGHT SPOTS ONTO A SURFACE

DISCLOSURE OF THE INVENTION

The present invention relates to a device for projecting light spots onto a surface.

More particularly, the present invention relates to a device of said type, which allows light spots having a shape and size which are constant on a plane or curved surface to be projected, at a varying distance and slope.

The projection of light spots onto surfaces is particularly, though not exclusively, applied in apparatuses for measuring human visual range, in particular in the apparatuses called "perimeters".

In these instruments the projection surface is a white hemispherical dome, at the center of which the patient's eye is to be placed.

Consequently, the system for projecting the spots onto the hemispherical dome turns out to be off centre.

As is well known, an accurate measurement of the visual range is of a great importance in ophthalmology, in the diagnosis and in the "follow-up" of several diseases, particularly in glaucoma.

Visual range is the visibility threshold in the various spatial directions with respect to the stared point.

During the examination of the visual range, a patient has to fix his eyes on a point at the center of a white hemispherical dome upon which luminous stimuli, or light spots, are projected from the periphery to the center of the hemispherical dome.

In the "kinetic" perimetry, the patient must press a button as soon as he sees a stimulus which moves from the periphery to the center of the visual range, whereas in the "static" perimetry static stimuli of a higher and higher brightness are projected until the patient presses the button.

The combination of the "visual points" on the whole range makes up a map of the visual range.

In Goldmann's perimeter, realized in 1945, which is still referred to as a standard, the hemispherical dome has a 33 cm radius and light spots of 0.01 to 1000 Apostilb, having surfaces of 1/16, ¼, 1, 4, 16, 64 mm² (spot: O, I, II, III, IV and V) are projected onto the ground, which is uniformly lit at 31.5 Apostilb. An arm pivoted on the vertical axis of the hemispherical dome, which turns behind the patient's head, brings a lens so inclined and orientable as to be able to project the light spot onto any point in the hemispherical dome, while keeping at the same distance and slope with respect to its surface. As a consequence the light spot results always to be elliptic, but of a constant shape and size, and the projector does not require a continuous focusing.

Computer-controlled automatic perimeters have been realized, based upon the same principle of Goldmann's one, in the subsequent developments of these apparatuses.

The main problems found in their realization are pertinent to the driving, due to encumbrance, and to the displacement of the projection mechanism from the right to the left side. Some examples as regards the above are the perimeter PERIKON Optikon, and patents U.S. Pat. No. 3,414,348, U.S. Pat. No. 4,145,123, U.S. Pat. No. 4,260,227 and U.S. Pat. No. 3,664,732.

Subsequently, in many perimeters, the projection criterion of Goldmann has been abandoned for the lighter systems, which comprise a movable mirror housed in the hemispherical dome out of the visual range, generally above the head of the patient, as for instance in the patents EU 0,242,723, U.S. Pat. No. 4,561,738 and in the perimeters Octopus and Squid. Owing, however, to the different distance between this mirror and the various points of the dome, and to the oblique incidence of the projected ray onto its surface, the light spots which are obtained with these devices haven't a constant shape.

Some perimeters in which a larger dome has been adopted, out of Goldmann's standard, have been realized, such as the perimeters Octopus Interzeag, in order to reduce such shortcoming to a minimum.

Still in other perimeters, as for instance the perimeter Bausch & Lomb FIELDMASTER 5000, fewer mirrors to put away the projector have been used, and the orientable mirror has been placed almost in contact with the forehead of the patient, in order to reduce the relative differences of the path of the beam. The problem has been however so added of a lower light yield of the projector and therefore of the necessity for employing more powerful lamps, fans, etc.

In such perimeters the light beam passes through holes of not a negligible size, located in the visual range, to contain the size of the orientable mirror.

The more recent perimeters are generally magnifycation-and spot-focusing-compensated.

In a few instances (U.S. Pat. No. 4,561,738, Humoured) the well-known property of a telescope of having a magnification ratio between the object and the image which is equal to the ratio between the two lenses and is independent of distance is exploited, by arranging the object-light spot in the conjugate position with respect to that of the projected image.

In another patent (Patent EU 0,242,723, Techna Vision) a double couple of movable mirrors at 45° is interposed, which compensates for the differences of the optical path, keeping at the same time either magnification and focusing.

Either system, however, does not take into account the fact that the light spot on an oblique surface turns out to be distorted.

Because the projectors of the perimeters realized according to the latest patents have a projection head which in definitive is larger and more displaced off the center than in the preceding perimeters, in a few points the light spot results to be much more distorted than in other points, with a change in the surface of the 20% and more.

Moreover, the particular realization of most projectors described heretofore limits the application thereof to the only static or kinetic perimetry, and such projectors often result to be slow or noisy, with the prejudice of the foreseeability of the stimulus, which makes the test's result less reliable.

Finally, the projectors of the automatic perimeters heretofore realized do not provide any system that allows the intermittency of the light to be regulated, to measure the critical frequency of fusion of the patient in the various points of the visual range.

Such a type of test (flicker perimetry), though it is ascertained that it would furnish a useful information for the diagnosis of glaucoma, has always relied upon instruments that do not guarantee standard or reproducible test conditions.

In view of the above-mentioned problems, the Applicant suggests to realize a device for projecting light spots which is able to obviate all the mentioned drawbacks.

The primary object of the present invention is to provide a device of said type which is able to project circular light spots of constant shape and size, by virtue of being endowed of mechanisms compensating for the shape and the size of the light spot themselves projected in the dome indpendently of the the distance and of the inclination of the latter with respect to the projector itself.

It is still an object of the present invention to provide a device which is adoptable on perimeters realized either with a telescopic projection system, or with a double couple of movable mirrors.

A further object of the present invention is to realize a device that allows either the kinetic and the static perimetry to be carried out.

Another object of the present invention is to obtain a device endowed with a system for regulating the intermittency, to measure the critical frequency of fusion of the patient in the various points of the visual range.

It is therefore a specific object of the present invention a device for projecting light spots onto a surface, which device comprises a device for producing and concentrating light, a pierced member, which is movable before said device and is endowed with means for selecting a hole to be aligned with the light, an assembly of lenses and mirrors and a projection head for projecting the light onto a surface, and a shutter member, which regulates the projection of the light beam itself, in which device means for orienting said pierced member around the vertical axis passing through the center of the selected hole and means for orienting the same pierced member around the horizontal axis passing through the center of the selected hole are provided; the orientation and the position of the pierced member, as well as the selection of the hole and of the orientation of the projection head being obtained by a computer.

Between the device for generating and concentrating the light and the pierced member a circular filter may be provided, which is preferably inclined with respect to the axis of the light beam, while a disk with filters may be provided between the pierced member and the shutter, or between the device for generating and concentrating light and the pierced member, both being controlled by the computer.

In particular, according to the present invention, said circular filter may consist of a mirror photo-etched with a graphic screen according to a logarithmic angular function.

Moreover, said disk with filters may provide two neutral filters of a reciprocally double logarithmic density, in order to raise the light spot's excursion up to 50–60 dB.

In a preferred embodiment of the device according to the present invention, said pierced member, preferably comprised of a pierced disk, is arranged on a carriage, movable by means of a first stepper motor, and is endowed with a second stepper motor for selecting a hole.

Two structures are in addition arranged on said movable carriage, respectively endowed with a third and a fourth stepper motor, for orienting the pierced member with respect to the vertical axis and to the horizontal axis, passing through the center of the selected hole, respectively.

The third, the fourth and the second stepper motors are assembled on structures realized so that each one moves the preceding. The order of the sequence of the movements may, obviously, be changed.

Furthermore, mechanical reductions which increase the light spot resolution may be provided.

Each of the provided stepper motors is endowed with a recalibration stop.

The assembly of lenses and mirrors may be comprised of a first lens, arranged immediately after the pierced member, of two reflection mirrors, and of a second lens, the two lenses being arranged at a distance corresponding to the addition of their focal lengths.

As an alternative, the assembly of the lenses and mirrors may comprise a single lens, it also arranged immediately after the pierced member, two reflection mirrors and at least a double couple of movable mirrors at 45°, to compensate for the differences of optical path.

The projection head, endowed with a protective fairing and housed, preferably, in a high position with respect to the surface of projection, may comprise a horizontally orientable mirror, by means of a first DC motor and of a chain and gear system, and vertically, by means of a second DC motor and of a system with a steel wire and recovery springs, and two potentiometers which control the achievement of the desired position.

The device for generating and concentrating light will be preferably made up of an halogen lamp and of a condenser and of one or more lenses.

The shutter of the device according to the present invention, arranged downstream of the pierced element, endowed with a command logic and driven by a DC motor, provides a turnable blade, by action of said motor, and two fork light couplers which are covered or uncovered by the blade itself, the blade being realized asymmetrically or the two light couplers being arranged asymmetrically.

In particular, said DC motor is driven by a bridge of four transistors or by two complementary symmetry, power operational amplifiers.

The command logic provides three input signal and two signals returning from said light couplers.

BRIEF DESCRIPTION OF THE DRAWING

The present invention will be now described according to preferred embodiments thereof with particular reference to the figures of the enclosed drawings, in which:

FIG. 1 shows, schematically, the principle of the operation of a classic projector;

FIGS. 2a, 2b and 2c show schematically the principle of operation of a telescopic projector;

DETAILED DESCRIPTION OF THE PREFERRED EMBODIMENTS

Figure 4:
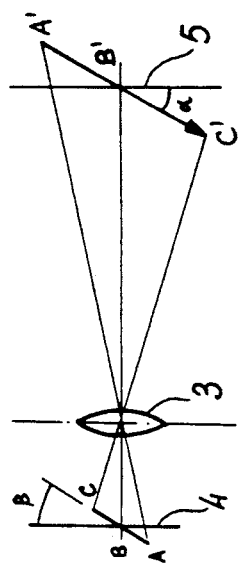
FIG. 4 shows schematically the principle on the basis of which the device according to the present invention operates.

FIG. 1 shows a classic projector. The condenser 1 projects the filament of the lamp 2 onto the lens 3. The subject 4 to be projected is at a distance D1 from the lens 3, which is conjugate to the distance D2 between the lens 3 and the projected image 5, that is to say such as:

$$1/D1 + 1/D2 = 1/F \qquad (1)$$

where F is the focal length of the lens 3. The magnification of the projected image 5 with respect to the subject is:

$$I = D2/D1 \qquad (2)$$

If D2 increases, it will be necessary to change D1 according to (1), in order to keep the image focussed, and the magnification increases according to (2).

In FIG. 2a, the lens 3 has been substituted with a telescope, i.e. with two lenses (6, 7) at a distance equal to the sum of the focal lengths F1+F2. If the subject 4 is close to the first lens 6, according to (1) the image 5 will be focussed at a distance:

$$1/D2 + 1/(F1 + F2) = 1/F2 \qquad (3)$$

$$\begin{bmatrix} D1 = 0 \\ D2 = F2/(1 - F2/(F1 + F2)) \end{bmatrix}$$

and the magnification results to be:

$$I = D2/(F1+F2) = F2/F1 \qquad (4)$$

If, on the contrary, the subject 4 is in the focus of the first lens 6 (FIG. 2b) the rays between the two lenses turn out to be parallel and the second lens 7 focuses the image 5 at the distance:

$$\begin{bmatrix} D1 = F1 \\ D2 = F2 \end{bmatrix} \qquad (5)$$

The linear interpolation between the two limits (3) and (5) gives:

$$D2 = (F2 + F2^2/F1) - (F2/F1)^2 * D1 \qquad (6)$$

that can be checked easily either for (3) and for (5). The magnification keeps however equal to:

$$I = F2/F1 \qquad (7)$$

A more rigorous proof of (6) and (7), easily obtained on the basis of the similitude of the triangles in FIG. 2c, is herein omitted.

Figure 3:
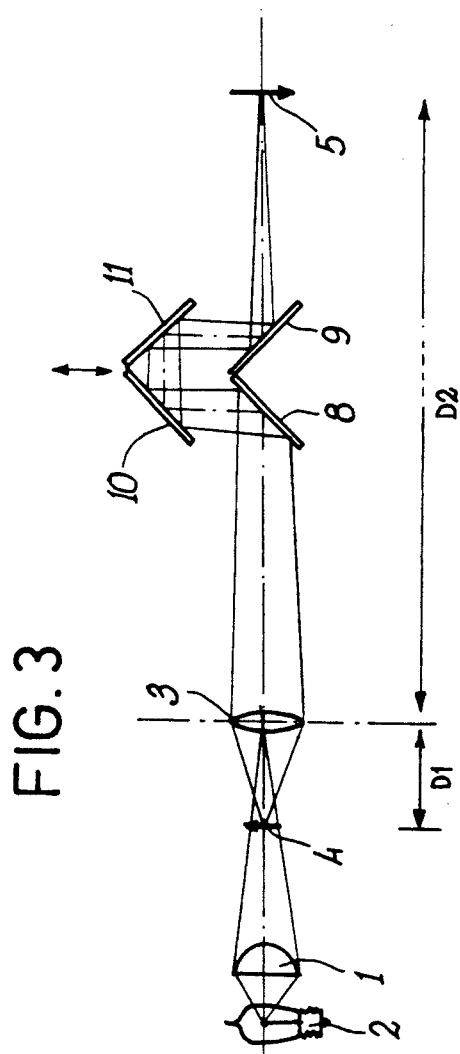
FIG. 3 shows schematically the principle of operation of a projector with a double mirror system.

In the case of FIG. 3 the whole optical distance between the lens of the projector 1 and the image 5 of the light spot, D2, is constant, being continuously compensated for by the mirrors 8, 9, 10, 11. The magnification ratio is given by the ratio D2/D1.

If the projection surface isn't at right angles with respect to the light beam emitted by the projector, it suffices to bend the subject in a direction parallel to the surface itself to compensate for the geometric proportions, as is demonstrated by the geometric proportions between the similar triangles in FIG. 4.

It is necessary to find a compromise between the magnification ratio and the focusing. Indeed, it is apparent from FIG. 4 that the point of the image closest to the lens 3, corresponds to that which is closest to the subject 4, and vice-versa, in opposition to what is requested from (1).

Figure 5:
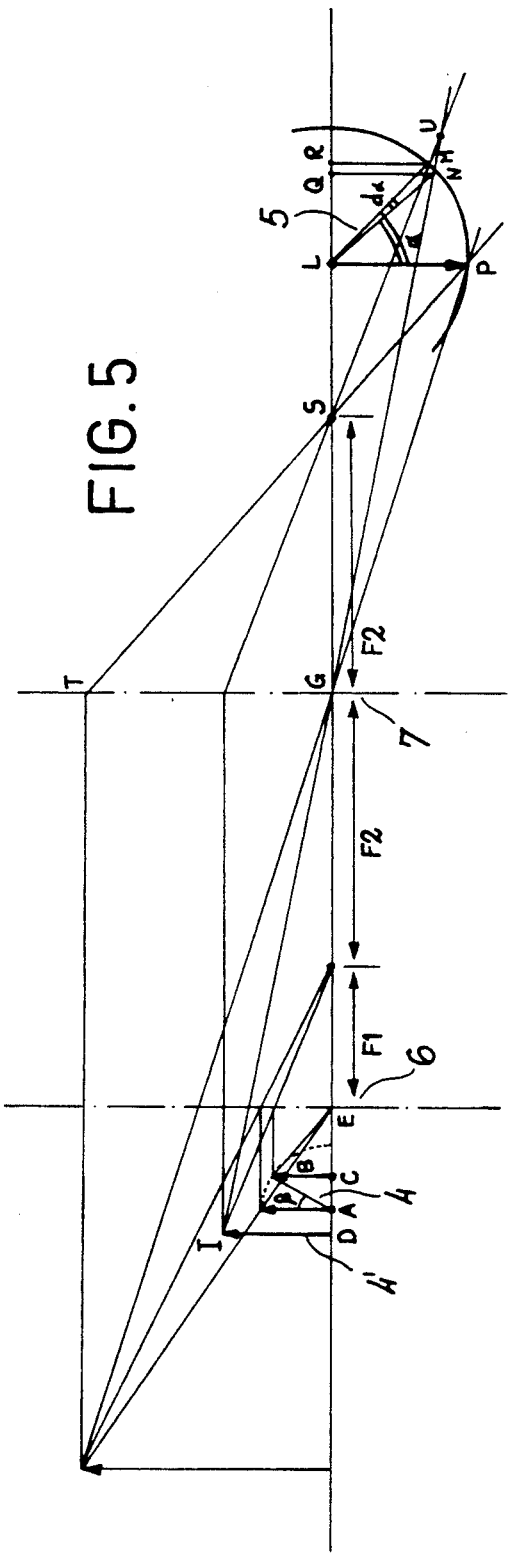
FIG. 5 shows schematically the principle of operation of the device according to the present invention, with a telescopic optics.

Employing also a projector with a telescopic optics, the image distortion may be compensated for by inclining the light spot disk, but in the opposite sense, as results from (6) and from FIG. 5.

However, it is seen from these figures that the horizontal movement of a point is magnified in the focused projected image, by a factor $(F2/F1)^2$, whereas the lateral movement (magnification (7)) by a factor $(F2/F1)$. Therefore it should be $F2 = F1$ for a rigorous compensation.

Because on the contrary a higher ratio (e.g. 2:2) is useful to contain the range of the spot disk (¼ of the range in the optical path D2), it will be demonstrated that for a spot small with respect to the focal distances, the depth of field is such that the two inclinations turn out to be, with a good approximation, equal and opposite, i.e.:

$$\alpha = \beta \qquad (8)$$

Proof of (8):

Let AB, AE, $\beta$, F1, F2 be given from the graph in the FIG. 5; it will result:

$$CE = AE - AB * \sin(\beta) \qquad (9)$$

$$BC = AB * \cos(\beta) \qquad (10)$$

$$BC/CE = DI/DE \qquad (11)$$

$$BC/F1 = DI/(DE + F1) \qquad (12)$$

By substituting for DI from (12) in (11), and developing with respect to DE:

$$DE = DI*CE/BC = (BC*(DE+F1)/F1)*(CE/BC)$$

$$F1*DE = CE*DE + F1*CE$$

$$DE = (F1*CE)/(F1 - CE) \qquad (13)$$

By the proportion between the triangles IDE and BCE:

$$ID/BC = DE/CE$$

$$ID = (F1*CE)/(F1 - CE)*BC/CE = (F1*BC)/(F1 - CE) \qquad (14)$$

The two rays which come out from the virtual image I of the point B, which are represented in the figure, intersect the circle through P center L, in the two points N and M. The angle $\alpha$ is that for which the image of AB, projected onto a plane surface passing through LN or LM, keeps the length LP, and the closeness between N and M gives a measure of the field depth of the projection.

By similitude between the triangles NQG and GDI:

$$LG + AB^*(F2/F1)^* \sin(\alpha))/(AB^*(F2/F1)^* \cos(\alpha)) = (F1 + F2 + DE)/ID$$

$$\cos(\alpha) = ID/(F1 + F2 + DE)^*(\sin(\alpha) + (LG/AB^*)(F1/F2)) \quad (15)$$

For light spots small with respect to the focal lengths it results (by substituting for 13, 14, 9, 10 in (15)):

$$\lim_{AB \to 0} \cos(\alpha) = \lim_{AB \to 0} \left[ \frac{F1^*AB^*\cos(\beta)^*(\sin(\alpha) + (LG^*F1)/(AB^*F2))}{(F1 - (AE - AB^*\sin(\beta)))\left(F1 + F2 + \frac{F1^*(AE - AB^*\sin(\beta))}{F1 - (AE - AB^*\sin(\beta))}\right)} \right] =$$

$$\cos(\beta)^*LG/[(F2 + F2^2/F1) - (F2/F1)^{2*}AE]$$

and being, for (6), $LG = (F2 + F2^2/F1) - (F2/F1)^{2*}AE$, the (8) has been proved.

Analogously, by the similitude between the triangles MRS and SGT, one obtains:

$$\cos(\alpha) = ID/F2^*(\sin(\alpha) + (LG - F2)/AB^*(F1/F2)) \quad (16)$$

where the limit for $AB \to 0$ gives again the (8).

In practice, by solving (15) and (16) with the following values (in mm): $F1 = 120$; $F2 = 240$; $AE = 10$ to 60; $AB = 5$ (light spot V); $\beta = 0°$ to $20°$, the values related in the following Table I for the angle $\alpha(\beta)$ and the defocusing $d\alpha$ are obtained in the worst case:

TABLE I

| Beta | d(Alpha) | Alpha |
|---|---|---|
| 1 | .106 | 1.478 |
| 2 | .303 | 2.827 |
| 3 | .414 | 3.987 |
| 4 | .500 | 5.097 |
| 5 | .567 | 6.177 |
| 6 | .621 | 7.239 |
| 7 | .666 | 8.287 |
| 8 | .703 | 9.326 |
| 9 | .734 | 10.357 |
| 10 | .759 | 11.382 |
| 11 | .781 | 12.402 |
| 12 | .800 | 13.418 |
| 13 | .816 | 14.432 |
| 14 | .829 | 15.442 |
| 15 | .840 | 16.450 |
| 16 | .849 | 17.456 |
| 17 | .857 | 18.460 |
| 18 | .863 | 19.462 |
| 19 | .868 | 20.463 |
| 20 | .871 | 21.462 |

By approximating such values with the (8) the size error is lower than the 9% about, the field depth allows a focusing better of the 5%. Both values fall below the 2% with the light spot III.

A device according to the present invention is represented in the FIGS. 6 to 9 in the embodiment with a telescopic projector.

The condenser 12 concentrates the light produced by a halogen lamp 13 onto the spot disk 14. The latter is movable in the space between the condenser 12 and pin 15 on a carriage 16 which is moved by a motor 17.

The movement of the carriage 16 is computed on the basis of the relation (6), by a computer, not represented, which computes the distance between lens 18 and the cupola 19 in a point-by-point way.

The image of the spot, selected by the motor 20, is projected by said lens 18, arranged at a distance equal to the sum of the focal lengths, and returned back to the mirrors 21, 22 and 23 into the dome 19.

Three stepper motors 20, 24 and 25, of small sizes, each being arranged on a structure that is moved by the other motor, are arranged on the carriage 16.

In particular, the motor 24 of SAG or horizontal inclination determines the rotation of the spot selected by the motor 20 in the horizontal sense, around the vertical axis passing through the spot, whereas the TILT or vertical inclination motor 25 rotates the spot in a vertical direction, while keeping the center thereof aligned with the axis of the light cone coming from the condenser 12.

Figure 6:
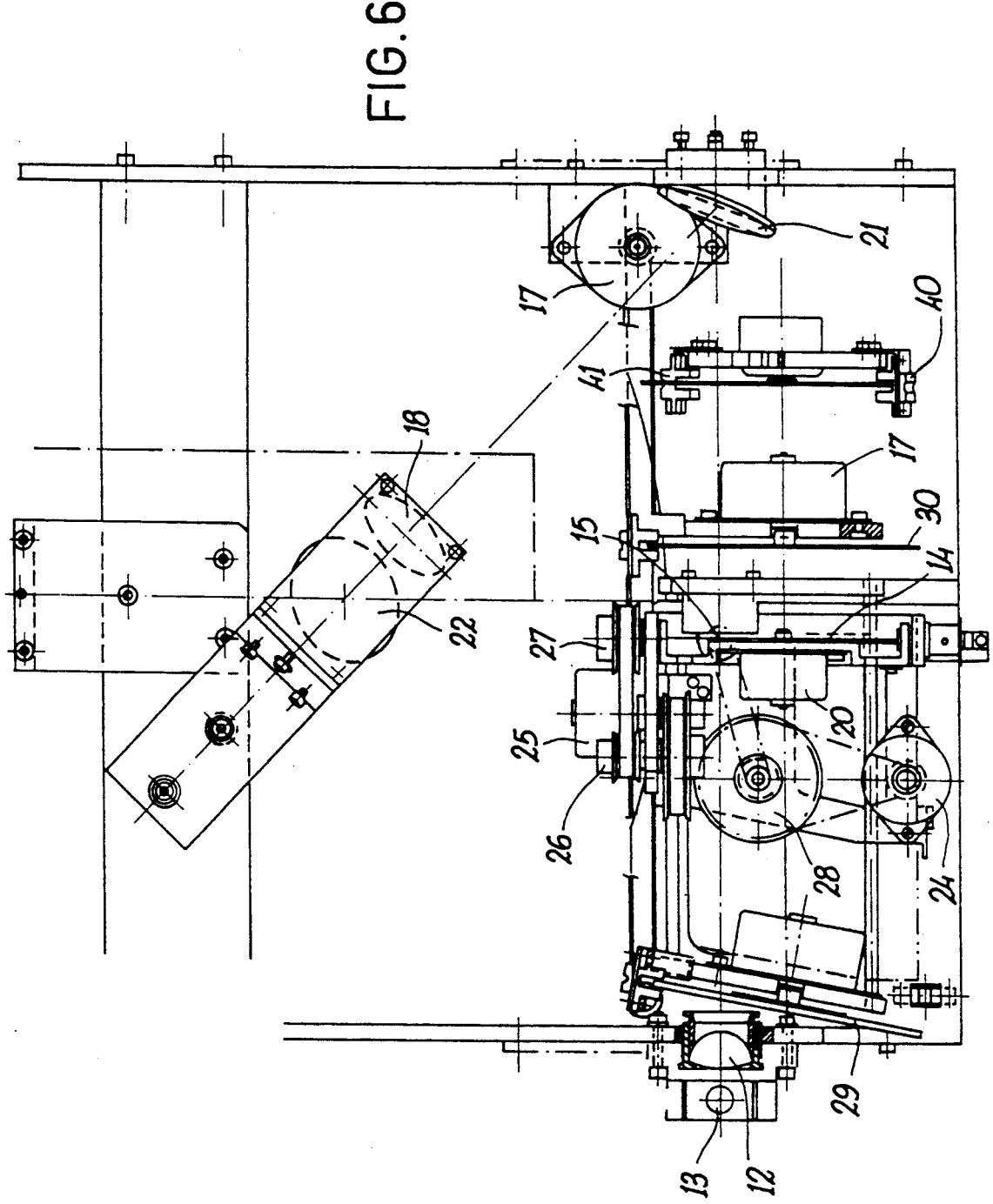
FIG. 6 is a plan view of the device according to the present invention.
Figure 7:
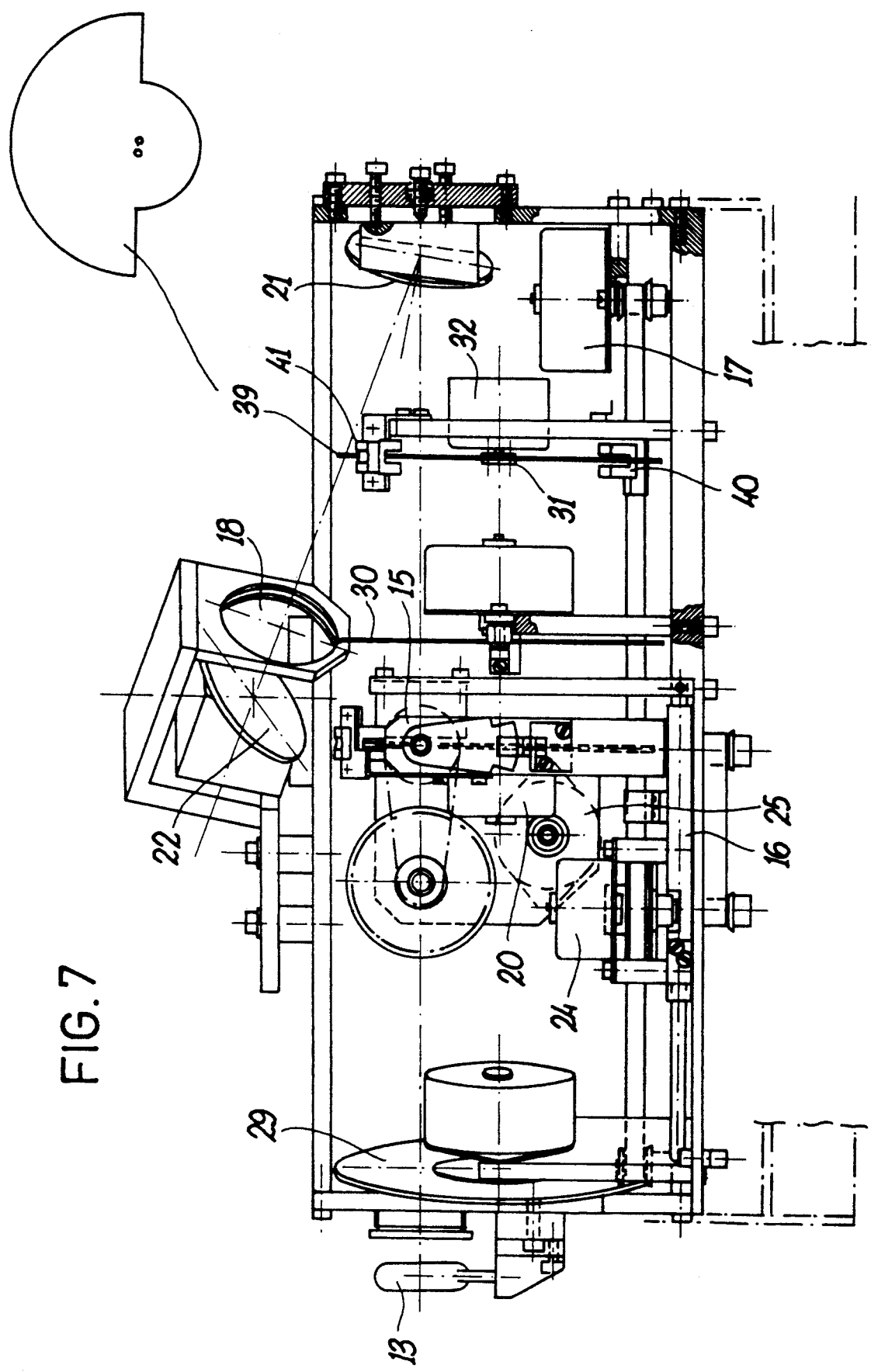
FIG. 7 is a side view of the device according to the present invention.

The resolution in the orientation of the spot disk 14 is incresed by providing reduction wheels 26, 27 and 28. The two movements necessary to orient the disk are performed by motors 24 and 25 (see FIG. 6). Motor 24 is belted to wheel 28 which is in turn belted to move pin 15 in the horizontal direction as illustrated in FIG. 6. Motor 25 is belted to move wheel 26 which is belted to move wheel 27. By means of this transmission, the motor 20 is made rotatable on a vertical plane around the axis of the wheel 27. In other words, motor 24 moves motor 20 as well as the groups 25, 26 and 27 in horizontal direction, while motor 25 moves the motor 20 in vertical direction through the wheels 26 and 27. Said orientation is computed on the basis of (8), in the two senses, and of the incidence angle of the beam projected onto the dome, in a point-by-point way, taking into account the rotations impressed to the beam by the three mirrors 21, 22 and 23 also.

In the illustrated embodiment, the maximum provided rotation is of about 0° to 20° of SAG and −20° to +20° of TILT.

By means of a circular filter 29 and of the filters of the disk 30 the spot luminous intensity is controlled, in a range of about 20 dB. The filters of the disk 30 allow the color of the spot to be changed and the range thereof to be increased up to 50–60 dB by using two neutral filters of reciprocally double densities.

The circular filter 29 may be realized by employing a photographic emulsion or a metal deposited onto glass or polyester, though in this way it would malsupport the heat of the lamp, particularly in kinetic projections, and would be expensive.

Figure 10:
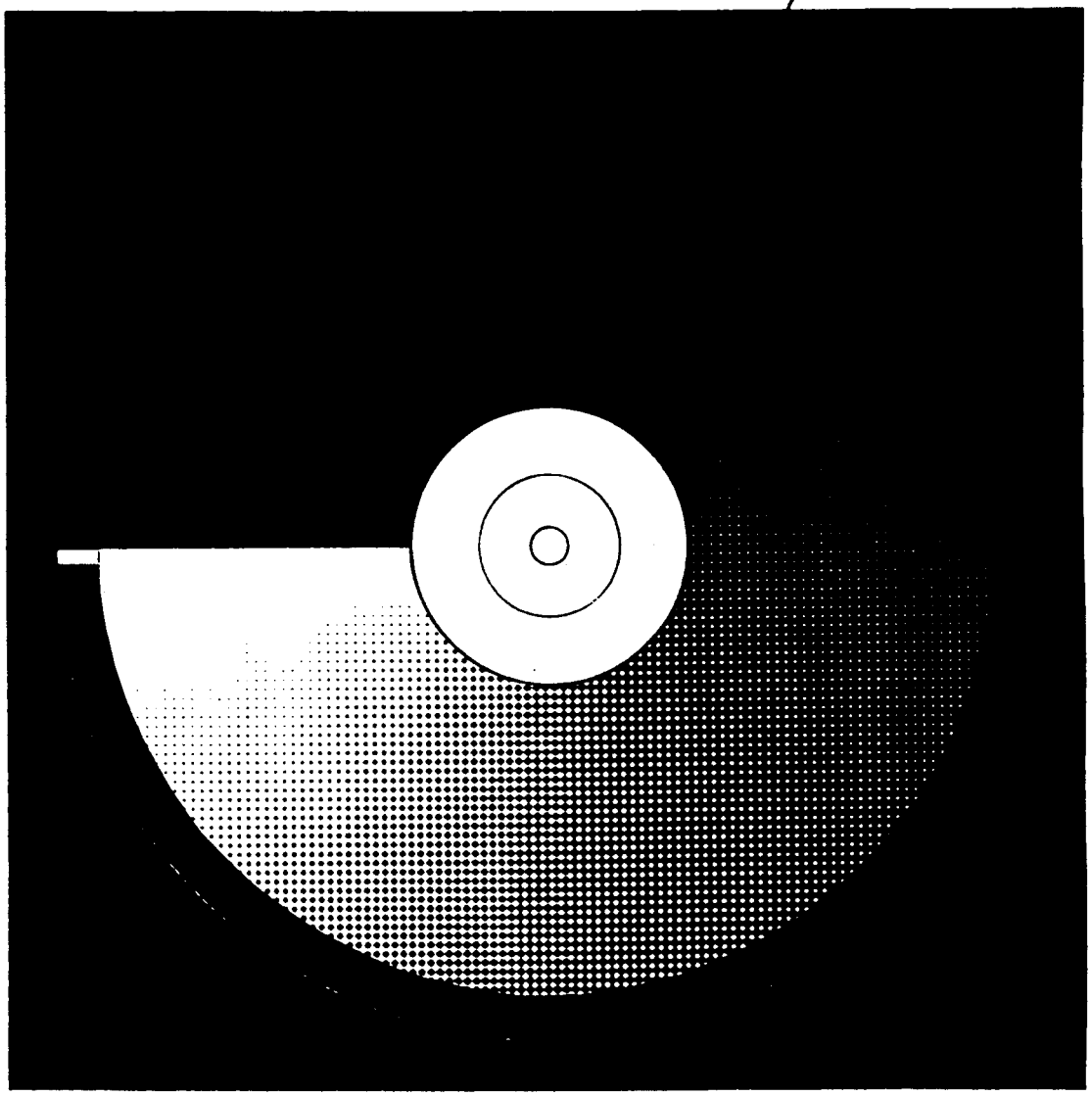
FIG. 10 shows a particular graphic screen to be employed in the device according to the present invention.

In FIG. 10 a graphic screen, shaded according to a logarithmic angular function, employed to photoetch a mirror that embodies the filter 29 is represented. This solution is adoptable as the filter 29 is interposed between the condenser 12 and the spot disk 14.

The light that has not been transmitted is reflected, so avoiding the need for a filter against heat.

Its slope avoids light, independently of how it is out of focus, being returned just on lamp's 13 filament.

The shutter 31, whose structure and operation will be shown and disclosed in the following, is moved by means of a low cost direct current motor 32.

Figure 8:
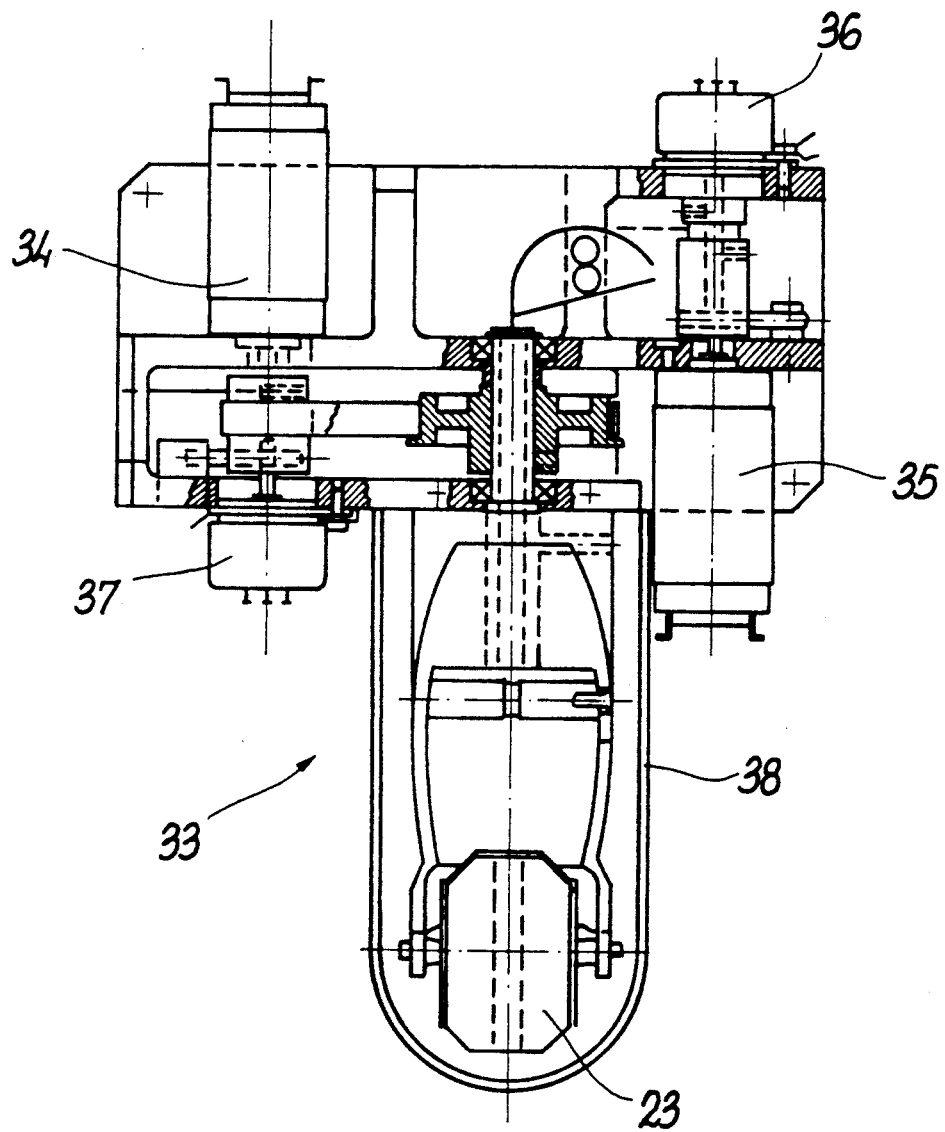
FIG. 8 shows the projection head of the device according to the present invention.
Figure 9:
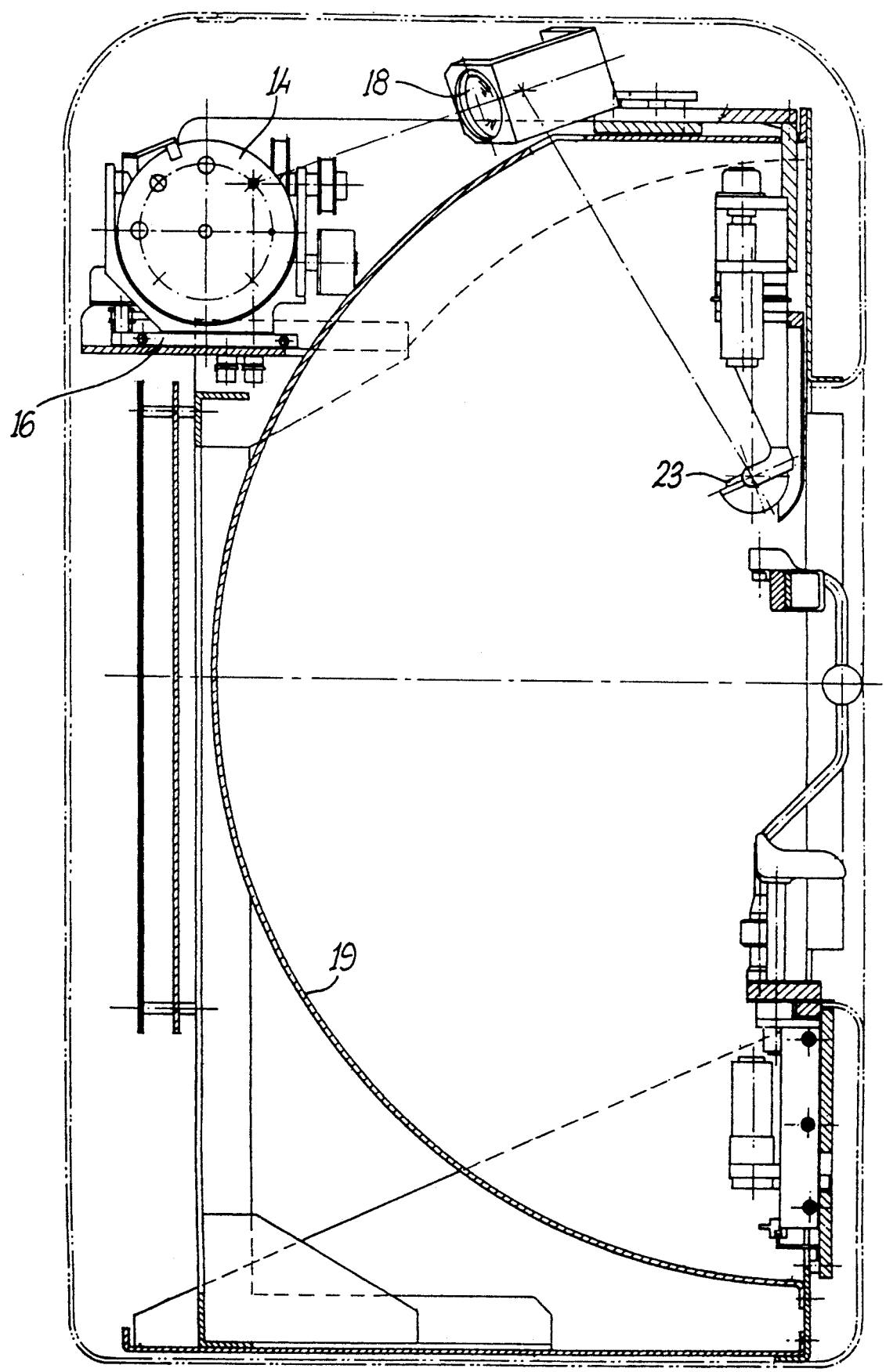
FIG. 9 shows a second side view of the device according to the present invention.

The projector head 33, see in particular FIG. 8, comprises a mirror 23 having such a shape, as to reflect the light beam into all the directions of the visual range and rotating horizontally by virtue of the motor 34, by chain and gears, and vertically, by virtue of the motor 35 and of a steel wire recovered by springs.

Two potentiometers 36 and 37 sense the orientation of the mirror 23, which potentiometers check the achieving of the angular position shown by the computer.

The two angles are computed as functions of the co-ordinates of the projection point into the dome 19, of the position of the mirror center and of the hole for inputting light.

A fairing 38 is also provided for, which protects the head of a patient from the contact with moving parts.

The projection head 33 preferably is housed in a high position on the dome 19 owing to the fact that the visual range is limited above to 60°-65°, which is a suitable angle for the hole for inputting light. If one had a greater angle, a larger mirror 23 would be necessary.

The shutter 31 is endowed with a blade 39 that may cover or uncover the light cone between the two lenses 15 and 18 dependently on being in a position in which fork light couplers 40 and 41 are both covered or both uncovered, because the blade 39 is realized in an asymmetrical way.

In case one wants the blade 39 to be realized in an asymmetrical way, it suffices to arrange the light couplers 40 and 41 asymmetrically.

In FIGS. 11 to 14 the shutter control circuit 31 and the logic of the operation thereof are shown.

Figure 11:
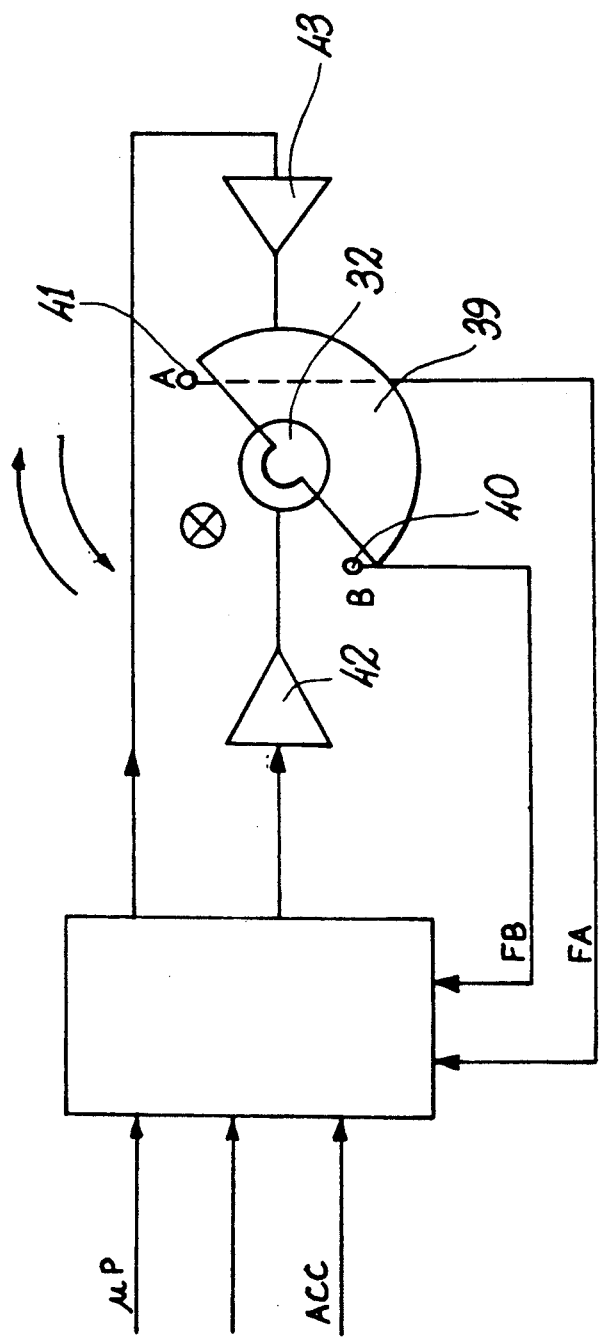
FIG. 11 shows a block scheme of the circuit which controls the light shutter according to the present invention.

The motor 32, that rotates the blade 39, is driven by a bridge of four resistors or by two complementary symmetry power operational amplifiers 42, 43, as depicted in FIG. 11.

A positive voltage (1) on the signal ORARIO and a negative one (0) on the signal ANTIORARIO are supposed to apply a clockwise couple, and viceversa, to the motor 32. A same voltage (1 or 0 applied to both) stops the motor.

The two signals, designated FA and FB, go high when the photoelectric cell 41 or 40 is uncovered and provide a "feedback" to keep the shutter 31 open if FA=FB=1 or closed if FA=FB=0.

The three signals designated with CHIU, uP and ACC, coming from the computer, control the operation of the shutter 31.

The logic is set forth in the following table II.

TABLE II

| Situation: | Inputs: | | | | | Outputs: | |
|---|---|---|---|---|---|---|---|
| | CHIU | μP | ACC | FB | FA | ORARIO | ANTIOR. |
| Open shutter: quiescent condition | 0 | 0 | x | 1 | 1 | 0(1) | 0(1) |
| counterclockwise feedback | 0 | 0 | x | 0 | 1 | 0 | 1 |
| Clockwise feedback | 0 | 0 | x | 1 | 0 | 1 | 0 |
| Closed shutter: quiescent condition: | 1 | 0 | x | 0 | 0 | 0(1) | 0(1) |
| counterclockwise feedback | 1 | 0 | x | 1 | 0 | 0 | 1 |
| clockwise feedback | 1 | 0 | x | 0 | 1 | 1 | 0 |
| (clockwise) Acceleration | x | 1 | 1 | x | x | 1 | 0 |
| (clockwise) deceleration | x | 1 | 0 | x | x | 0 | 1 |

1 = HIGH logic level
0 = LOW logic level
x = indifferently HIGH or LOW logic level
( ) = alternative logic level, on both outputs When $\mu P=0$ and CHIU=0, the "feedback" of the two local signals FA and FB keeps the shutter 31 open: an unbalance of the blade 39 to cover the photoelectric cell 40 and 41 produces a couple on the motor 32 which returns the blade 39 itself into an open position.

Analogously, when $\mu P=0$ and CHIU=1, the "feedback" of the two local signals FA and FB keeps the shutter 31 closed.

When $\mu P=1$, the automatic control of the photoelectric cells 40 and 41 is cut off, and the computer may accelerate or decelerate the motor (as a reference, in the clockwise sense), with the signal ACC being =1 or =0 respectively.

Figure 12:
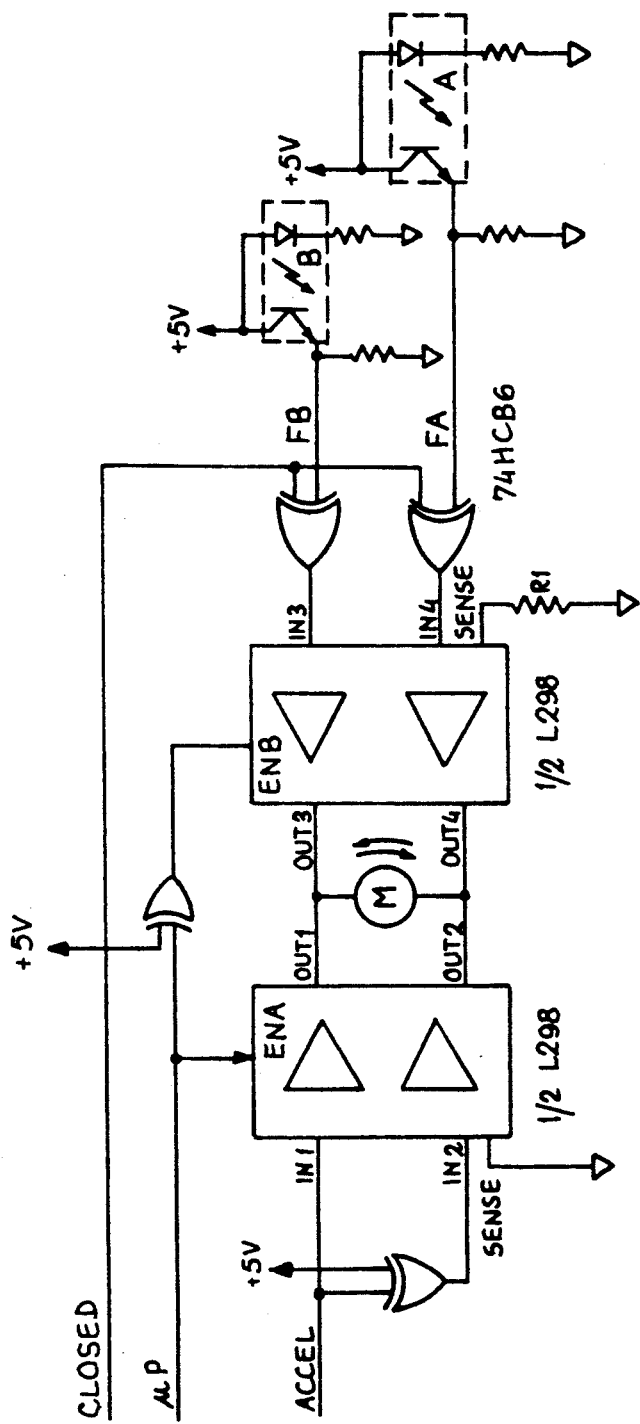
FIG. 12 shows an electric scheme of the circuit of FIG. 11.

The schematic in FIG. 12 shows an embodiment of the drive circuit with only two integrated circuits. The resistor 21 allows some electric current to be saved during static phases.

Figure 13:
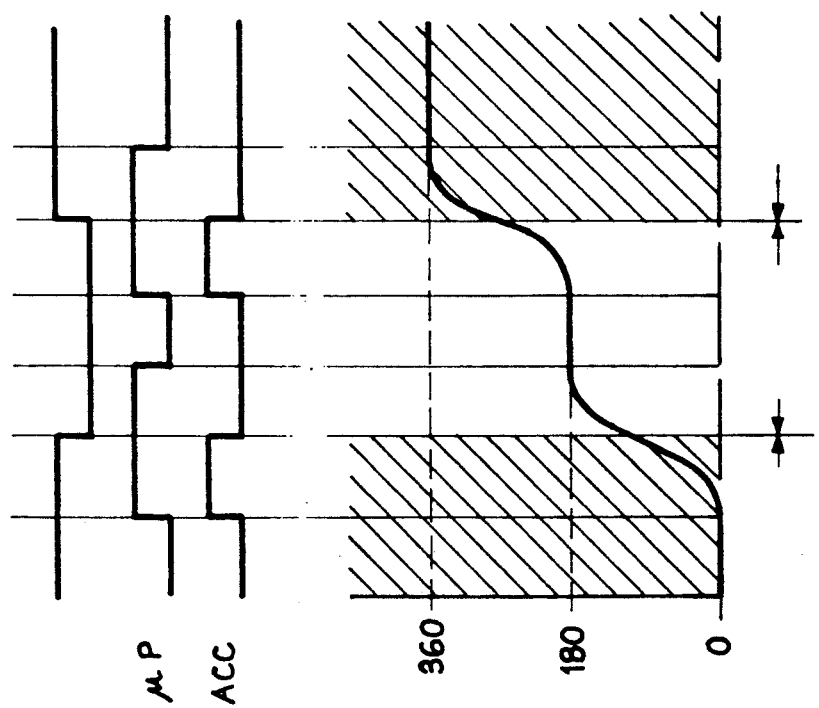

A typical signal sequence, for a static or a kinetic projection, is illustrated in FIG. 13, together with a graph of the angular position of the shutter 31. 5 phases are provided: the first acceleration and deceleration (of a fixed time interval), a pause (of an adjustable time interval), the second acceleration and deceleration (of a fixed time interval).

The light beam is crossed at the maximum speed, and opening times of 100 ms with beam transition of 5-10 ms may be easily obtained.

Figure 14:
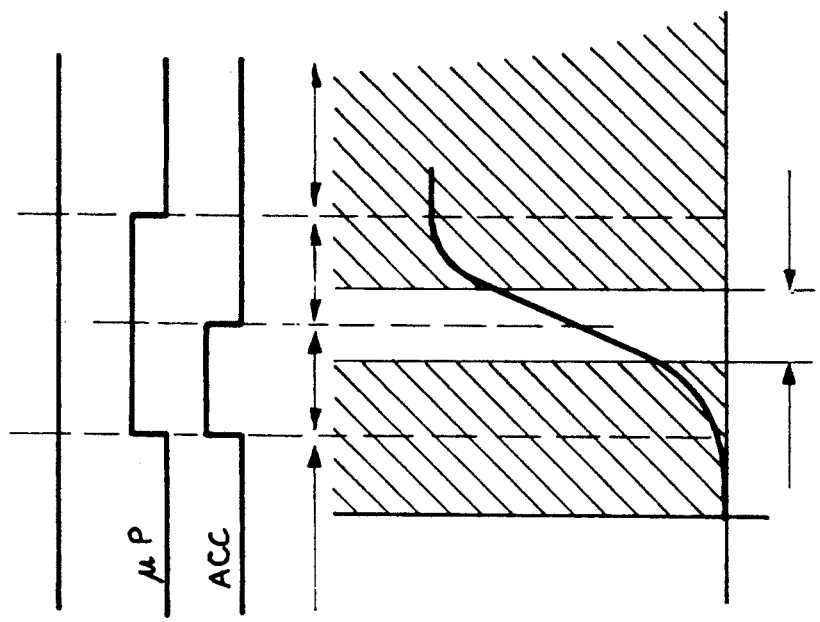
FIGS. 13 and 14 show the sequence of signals and the graph of the angular position of the light shutter.

Shorter times (up to about ¼ of the said time lengths) may be achieved by not stopping the motor 32, up to the boundary condition of two phases only (FIG. 14).

The shutter 31 may be utilized to modulate light at a prefixed frequency, by controlling the "duty-cycle" of two periodic acceleration-deceleration phases. The "feedback" for the rotation frequency may come to the computer from FA or FB indifferently. This application is particularly suitable in the flicker perimetry.

The present invention has been disclosed with specific reference to some preferred embodiments thereof, but it is to be understood that variations and/or changes may be made by those who are skilled in the art, without so departing from the scope of the enclosed claims.

We claim:

1. A device for projecting light spots onto a surface, comprising a device for generating and concentrating light, a pierced element, provided with a plurality of holes, movable before said device and endowed with means for selecting one of the holes to be aligned with the light, a lens and mirror assembly and a projection head for projecting light onto said surface, and a shutter member which regulates the projection of the light itself, characterized in that means for orienting the said pierced element around the vertical axis passing through the center of the selected hole and means for orienting the same pierced element around the horizontal axis passing through the center of the selected hole are provided, so that said pierced element can be inclined with respect to the optical path of the light of any possible angle in order to compensate the spot; the orientation and the position of the pierced element, as well as the selection of the hole and the orientation of the projection head, being performed by means of a computer.

2. A device according to claim 1, in which a circular filter is provided between the device for generating and concentrating light and the pierced element.

3. A device according to claim 2, characterized in that said circular filter is tilted with respect to the axis of the light beam.

4. A device according to claim 2 or 3, characterized in that said circular filter is comprised of a mirror etched photographically with a graphic screen according to an angular logarithmic function.

5. A device according to claim 1, in which a disk with filters is provided between the pierced element and the shutter element.

6. A device according to claim 5, characterized in that said disk with filters is endowed with neutral filters of a reciprocally double logarithmic density.

7. A device according to claim 1, in which said pierced element is composed of a pierced disk.

8. A device according to claim 1, characterized in that said pierced element is arranged on a carriage, which is movable by means of a first stepper motor, and is endowed with a second stepper motor for selecting the hole.

9. A device according to claim 8, characterized in that two structures are arranged on said movable carriage, respectively endowed with a third and a fourth stepper motor, respectively for orienting the pierced element with respect to the vertical axis and to the horizontal axis which pass through the center of the selected hole.

10. A device according to claim 9, in which said third, fourth and second stepper motor are mounted on structures arranged in such a way, as each of them moves the preceding one.

11. A device according to claim 8, characterized in that mechanical reductions are provided.

12. A device according to claim 8, characterized in that each one of said stepper motors is endowed with a recalibration stop.

13. A device according to claim 1, in which said lens and mirror assembly consists of a first lens, arranged immediately after the pierced element, of two mirrors for reflecting the light beam and of a second lens, the two lenses being arranged at a distance corresponding to the sum of their focal lengths.

14. A device according to claim 1, in which said lens and mirror assembly consists of a single lens, arranged immediately after the pierced element, of two reflection mirrors and of at least a double couple of movable mirrors at 45°, to compensate for the differences in the optical path.

15. A device according to claim 1, characterized in that the projection head is endowed with a protecting fairing and is housed high with respect to the protection surface.

16. A device according to claim 1, characterized in that said projection head comprises a mirror which is orientable horizontally by means of a first direct current motor and of a chain and gear system, and vertically by means of a second direct current motor and of a steel wire and recovery springs, and two potentiometers which check the achievement of the desired position.

17. A device according to claim 1, in which said device for generating and concentrating light consists of a halogen lamp and of a condenser with one or more lenses.

18. A device according to claim 1, characterized in that said shutter, arranged downstream of the pierced element, endowed with a command logic and moved by a DC motor, is endowed with a turnable blade, by the drive of said motor, and with two fork light couplers which are covered or uncovered by the blade itself, the blade being realized in an asymmetrical way or the two light couplers being arranged asymmetrically.

19. A device according to claim 18, characterized in that said DC motor is driven by a bridge of four transistors.

20. A device according to claim 18, characterized in that said DC motor is driven by two complementary symmetry power operational amplifiers.

21. A device according to claim 18, characterized in that said command logic provides three input and two signals send back from said light couplers.

* * * * *